United States Patent
Gomez et al.

(10) Patent No.: US 9,603,781 B2
(45) Date of Patent: Mar. 28, 2017

(54) SKIN CLEANING KIT

(71) Applicant: Next Wave Surgical LLC, Pompano Beach, FL (US)

(72) Inventors: Ricardo Alexander Gomez, Plantation, FL (US); Sandy Lawrence Heck, Los Angeles, CA (US); Eric William Conley, South Berwick, ME (US)

(73) Assignee: Coviden LP, Mansfield, MA (US)

( * ) Notice: Subject to any disclaimer, the term of this patent is extended or adjusted under 35 U.S.C. 154(b) by 782 days.

(21) Appl. No.: 14/017,706

(22) Filed: Sep. 4, 2013

(65) Prior Publication Data

US 2014/0069461 A1    Mar. 13, 2014

Related U.S. Application Data

(60) Provisional application No. 61/698,015, filed on Sep. 7, 2012, provisional application No. 61/867,472, filed on Aug. 19, 2013.

(51) Int. Cl.
| | |
|---|---|
| *A61K 8/02* | (2006.01) |
| *B65B 55/02* | (2006.01) |
| *A61Q 17/00* | (2006.01) |
| A61L 2/08 | (2006.01) |
| A61L 2/20 | (2006.01) |

(52) U.S. Cl.
CPC .......... *A61K 8/0208* (2013.01); *A61Q 17/005* (2013.01); *B65B 55/02* (2013.01); *A61L 2/081* (2013.01); *A61L 2/082* (2013.01); *A61L 2/087* (2013.01); *A61L 2/206* (2013.01)

(58) Field of Classification Search
CPC ..... A61K 8/0208; A61Q 17/005; A61L 2/081; A61L 2/082; A61L 2/087; A61L 2/206
USPC ................ 206/571, 225, 440, 366, 572, 569
See application file for complete search history.

(56) References Cited

U.S. PATENT DOCUMENTS

| | | | |
|---|---|---|---|
| 4,523,679 A | 6/1985 | Paikoff et al. | |
| 4,702,378 A * | 10/1987 | Finkel | A45C 11/00 |
| | | | 206/581 |
| 4,917,238 A * | 4/1990 | Schumacher | A47L 13/51 |
| | | | 206/223 |

(Continued)

FOREIGN PATENT DOCUMENTS

JP      2003-095815      4/2003

OTHER PUBLICATIONS

New Wave Surgical "Advanced Laparoscopic Care Kit" (packaging), #REF-21-345.

(Continued)

*Primary Examiner* — Chun Cheung

(57) ABSTRACT

The invention relates generally to sterile packaging kit of components to be used to clean an area of a patient's skin, and more particularly to a sterile kit for cleaning a patient's skin area in the surgical field, following a surgical procedure. The kit, in its most basic form, comprises an outer envelope containing at least one dry towel and at least one wetted towel in its own pouch, separated from the dry towel. The kit may further include a heating element which efficiently transfers heat to the wetted towel. The cleaning kit may also provide sterile bandages for use in covering closed surgical incisions, after postop cleaning of the skin the surgical field, using the wetted and dry towel of the kit.

21 Claims, 5 Drawing Sheets

(56) References Cited

U.S. PATENT DOCUMENTS

| | | | |
|---|---|---|---|
| 5,261,531 A * | 11/1993 | Nieves | A61F 13/5519 206/205 |
| 5,447,505 A | 9/1995 | Valentine et al. | |
| 5,785,179 A * | 7/1998 | Buczwinski | B65D 43/16 206/1.5 |
| 5,984,089 A * | 11/1999 | Dotson | B65D 75/5805 15/104.93 |
| D471,640 S | 3/2003 | McMichael et al. | |
| D471,641 S | 3/2003 | McMichael et al. | |
| D480,816 S | 10/2003 | McMichael et al. | |
| 7,673,754 B2 | 3/2010 | Wilson, Jr. et al. | |
| 8,173,146 B2 | 5/2012 | Leroy | |
| 2002/0104774 A1 * | 8/2002 | Hammond | A61F 17/00 206/570 |
| 2003/0029740 A1 * | 2/2003 | Caveness | A47K 10/02 206/210 |
| 2004/0004019 A1 | 1/2004 | Busch | |
| 2004/0007251 A1 | 1/2004 | Koenig et al. | |
| 2004/0088839 A1 * | 5/2004 | Maclean | A61F 17/00 27/21.1 |
| 2008/0054011 A1 * | 3/2008 | Grimard | B65D 75/5838 221/45 |
| 2009/0107876 A1 | 4/2009 | Bengtson | |
| 2009/0277915 A1 * | 11/2009 | Ferguson | B65D 81/3484 220/592.27 |
| 2011/0137222 A1 | 6/2011 | Masini | |

OTHER PUBLICATIONS

DuPont Medical Packaging, "Technical reference guide for medical packaging", pp. 1-38, Copyright 2005, DuPont Medical Packaining, Wilmington, DE 19805.

* cited by examiner

SKIN CLEANING KIT

CROSS REFERENCE TO RELATED APPLICATION

This application claims priority from provisional patent application Ser. No. 61/867,472 filed on Aug. 19, 2013 and entitled Patient Cleaning Kit and from provisional patent application Ser. No. 61/698,015 filed on Sep. 7, 2012 and entitled Laparoscopic Surgical Cleaning Kit with Optional Wound Dressing, the teachings of which are incorporated herein in their entirety, by reference.

FIELD OF INVENTION

This invention relates generally to sterile packaging of components to be used to clean a desired area of an individual's skin, and more particularly to a sterile kit for cleaning a patient's skin in the surgical field, following a surgical procedure.

BACKGROUND OF INVENTION

It is well known in the surgical art to package all of the components needed to carry out a given procedure in a kit which can be brought into a sterile operating field, opened and the sterile components of the kit utilized to carry out a given surgical procedure. For example, in carrying out a laparoscopic surgical procedure, a kit could include a plurality of tubular trocars. However, cleaning the wound following surgery has largely been improvised in the past based upon the judgment of the health care worker and whatever supplies are available. This has led to ineffective and improper patient cleaning.

In the case of the present invention, there is provided for the first time, a self-contained kit containing those components useful in cleaning the patient's skin following a surgical procedure. As surgeons and surgical nurses recognize, a patient's skin may have blood, body fluids, and antiseptic stains on the skin surface. In accordance with the present invention, there is provided a kit containing the necessary supplies in a sterile form for cleaning a patient's skin after surgery.

SUMMARY OF THE INVENTION

When cleaning the wound following surgery, the best results are achieved with multiple sterile cleaning articles that in the past were typically selected randomly from separate sources often without appropriate sterilization.

To overcome these and other deficiencies, the present invention provides a kit for washing away blood and other body fluids from a particular area of the skin surface, such as following a surgical procedure, which comprises an outer envelope that contains at least one Dry Fabric Towel and at least one sealed inner envelope containing a Wetted Fabric Towel, and where the outer envelope permits sterilization of the contents thereof through, but not limited to, application of one of gamma radiation, electron beam radiation, x-ray radiation or ethylene oxide gas.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention comprises an assembled kit, referred to as a Wet & Dry Kit, containing the necessary supplies for cleaning a patient's skin, such as in the area of the surgical field, following a surgical operation. The preferred embodiments could also be used in an Emergency Room or anywhere else in a hospital or healthcare facility where it becomes necessary to clean an area of a patient's skin.

The prior art process of cleaning a patient's skin after surgery requires the use of multiple supplies, which must be collected and assembled. This can waste time, waste money and result in inferior cleaning and/or dressing of the wound. Since selection of materials is left to the health care worker, results can vary widely. It is believed that there currently exists no prepackaged sterile kit with supplies designed specifically for cleaning a patient's skin after surgery. The present invention satisfies this unmet need by providing a prepackaged, disposable, sterile kit incorporating a Wet Fabric Towel for cleaning the patient's skin and a Dry Towel for drying the skin.

Figures 1A, 1B:
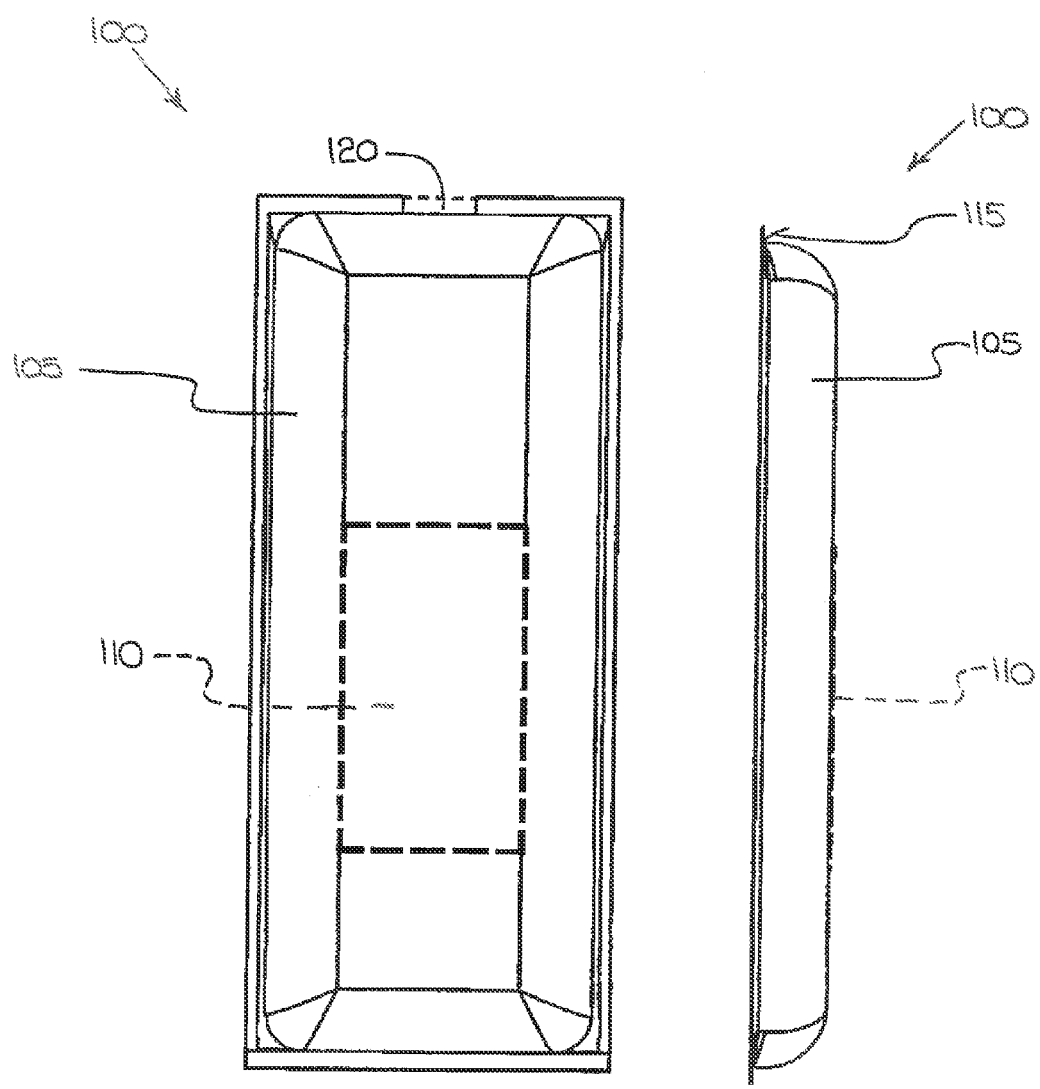
FIG. 1A illustrates an Isometric View of the Assembly Wet & Dry Kit in its present assembly, and packaging form.
FIG. 1B illustrates a Perspective side view of an assembled Wet & Dry kit.

FIG. 1A illustrates a Top Isometric view of the assembled Wet & Dry Kit, 100. FIG. 1B illustrates a side Perspective view of the assembled Wet & Dry kit, 100. In it we see an outer peel pouch or envelope 105 containing the kit's cleaning components. The outer peel pouch 105 comprises a transparent flexible plastic sheet with an identification label 110 adhered thereto. It is also possible to simply print the content information on the backing sheet 115. The outer peel pouch, 105 made of transparent flexible plastic sheet is bonded about its perimeter to a backing sheet 115, which may be made of a gas permeable material, preferably made of a non-woven, spun bond olefin, such as is sold under the trademark Tyvek® by the DuPont Corporation of Wilmington, Del. Peel pouches like the outer envelope 105 are commercially available from Oliver-Tolas Healthcare Packaging of Grand Rapids, Mich. A non-mating separation area 120 is located along the periphery, preferably along a top area of the assembled Wet & Dry Kit and is used to separate the transparent flexible outer peel pouch 105, from the backing sheet 115.

In FIG. 1B a Perspective side view of an Assembled Wet & Dry Kit 100, is illustrated showing separation between the transparent flexible outer peel pouch 105, and the backing sheet 115.

Figure 1C:
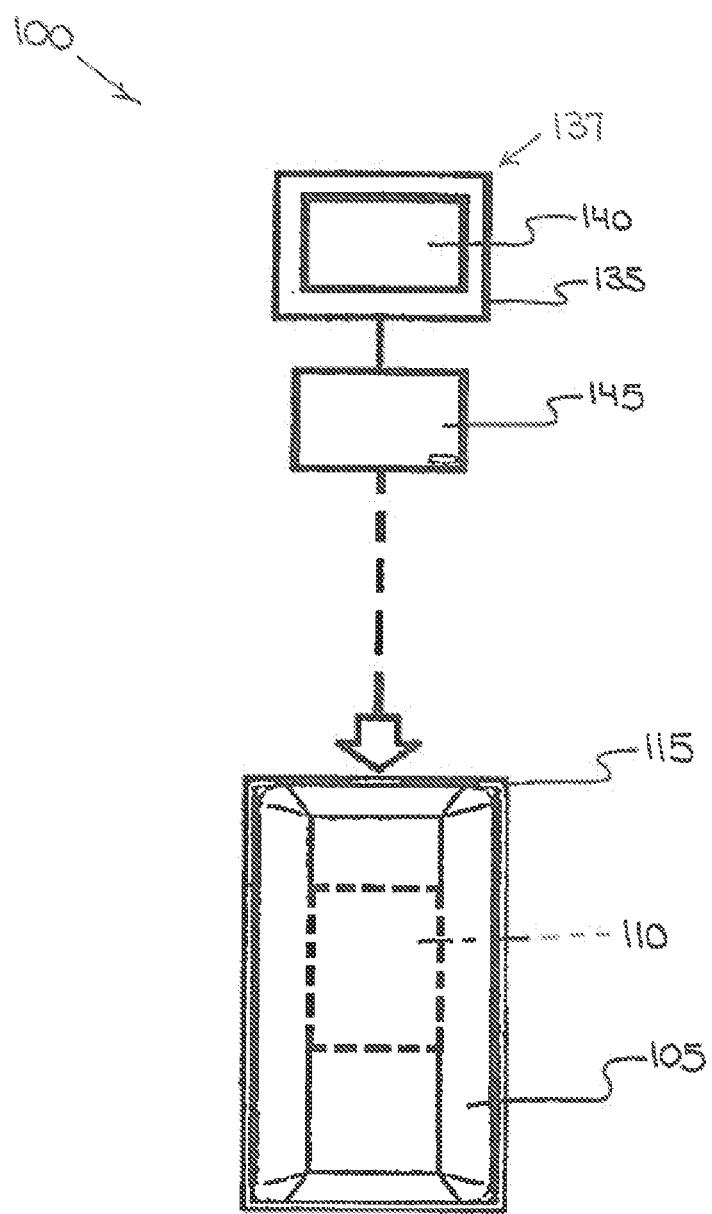
FIG. 1C illustrates an exploded isometric view of the basic configuration of the Wet & Dry Kit.

In FIG. 1C an exploded isometric view showing the content of the basic embodiment of assembled kit 100 to comprise at least one Dry Towel 145 and at least one Wet Towel Kit 137 comprising at least one Wetted Fabric Towel 140, sealed in an inner envelope 135; both items 137 and 145 being received within the sealable outer envelope 105 prior to sealing thereof. Just prior to use, the kit may be placed in a "warmer" (not shown), as are commonly found in an operating room.

The sealed inner envelope 135 containing the Wetted Fabric Towel 140, includes a wetting agent, the wetting agent being one of saline or plain water, but may also contain soap, surfactant, or other suitable detergent. The liquid wetting agent may further include an antibacterial solution. Without limitation, the Wetted Fabric Towel 140, may comprise any lintless material, such as microfiber fabric or a polyester/polyamide synthetic material of a size that is appropriate for cleaning a desired area of a patient's skin, for example, but without limitation, it may be 10 in.×12 in. and folded to fit within the smaller second or inner peel pouch 135 of the Wet Towel Kit 137. The Dry Towel 145 need not be in a peel pouch of its own when contained within the outer envelope 105. The Dry Towel 145 may be of the same material and be of the same size as the Wetted Fabric Towel 140. Once the Wet Towel Kit 137 and separate Dry Towel 145 have been sealed within the outer pouch 105, the assembled package may be subjected to a sterilization procedure. It has been found that gamma ray sterilization is optimum because the gamma rays readily pass through the outer envelope 105 and the contents therein, killing any pathogens that may be present. While gamma sterilization is preferred, ethylene oxide gas may also be used in that the preferred backing 115 on the outer peel pouch 105 is gas permeable.

Figure 2A:
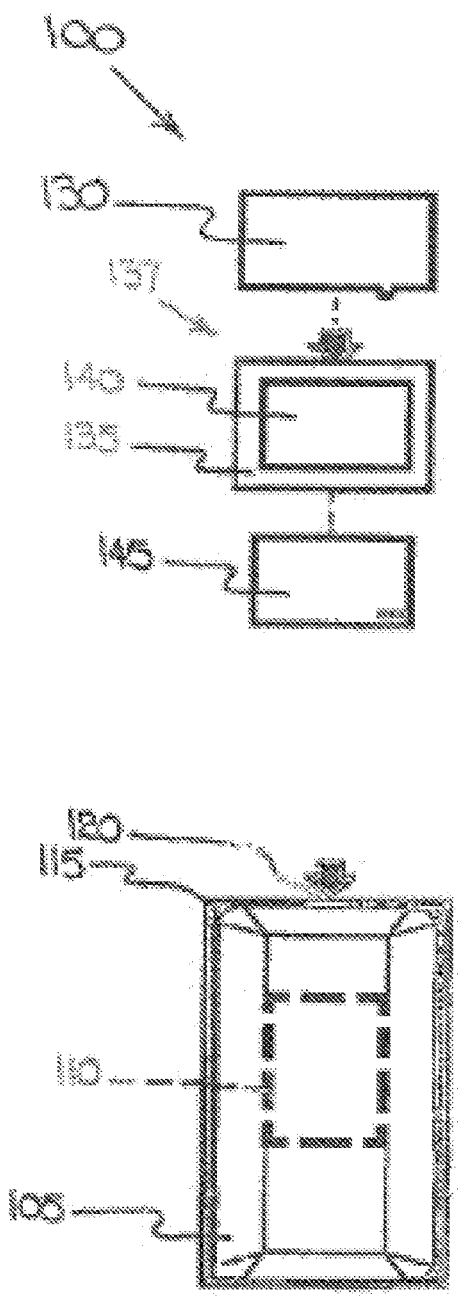
FIG. 2A illustrates an Exploded Isometric view of the elements of the Wet & Dry Kit.

In FIG. 2A an exploded Isometric view shows the contents of another embodiment of Assembled kit 100 removed from the outer peel pouch 105. The contents of the outer peel pouch 105 are seen to comprise at least one Wet Towel Kit 137 and at least one Dry Towel 145, with a heat pack 130 (described herein below) being sandwiched between two layers of the Wet Towel Kit 137, created by folding the Wet Towel Kit 137 in half.

Figure 2B:
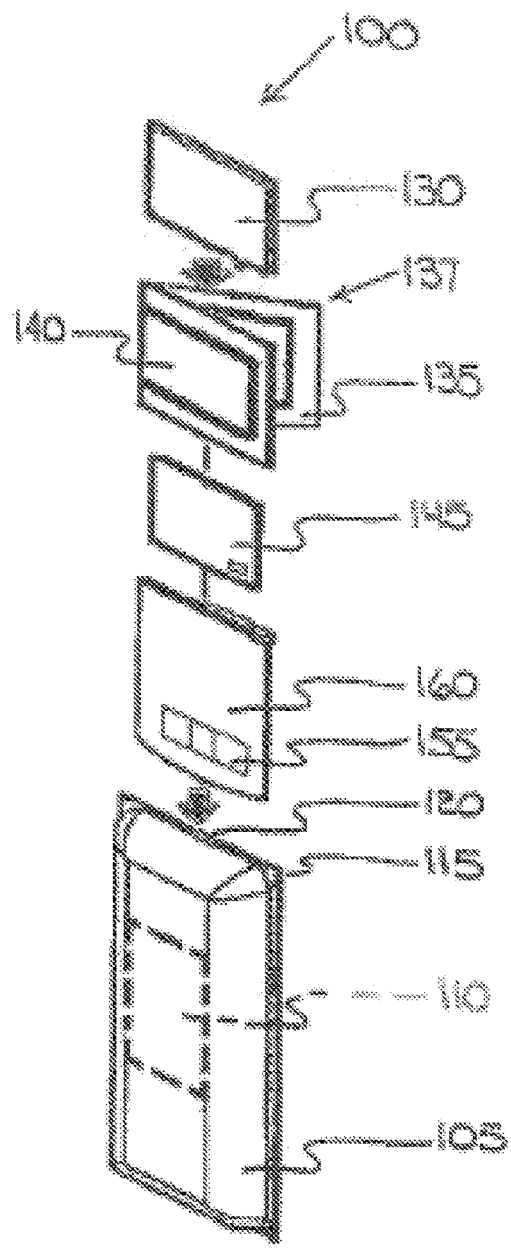
FIG. 2B illustrates an Exploded Perspective view of the elements of the Wet & Dry Kit, with optional Bandage Kit.

FIG. 2B is a perspective exploded view of a further embodiment of the Wet & Dry Kit, 100. By warming the Wetted Fabric Towel 140, it is not only more comfortable on the patient's skin, but also enhances the cleaning ability of the kit and reduces hypothermia. In use, the Outer Peel Pouch 105 will be opened by peeling it away from its backing layer 115, such that the components within the outer pack 105, may be deposited within the sterile field. Next, the inner sealed envelope 135 is opened and the Wetted Fabric Towel 140, contained therein may be used to wash blood and debris from the patient's skin. The Dry Fabric Towel 145 can then be used to dry the patient's skin.

In the preferred embodiments of FIGS. 2A and 2B of the Wet & Dry Kit 100, a heating pack, pouch, or element 130 is provided within the assembled kit 100. The heating element could generate heat electrically or, as in the preferred embodiment, would provide heating through an exothermic reaction. The heating pack 130 would preferably use a solution of Sodium Acetate Trihydrate ($CH_3COONa_3H_2O$), which reacts exothermically, crystallizing and generating heat which is transferred to the Wetted Fabric Towel 140. The heat generated ideally warms the Wetted Fabric Towel 140 to a temperature near or above body temperature, but below any dangerous levels (approximately 90-130 F). Various exothermic solutions may be used but in the preferred embodiment Sodium Acetate is used. Naturally the size of the heating element or pouch 130 will depend on the volume of fluid around the Wetted Fabric Towel 140. The heating solution pouch 130 incorporates an extended actuating tab 148 FIG. 2C, which, when activated causes a metal tab attached thereto which causes the Sodium Acetate Trihydrate to warm, warming the Wetted Towel kit 137 adjacent thereto, in known manner. The Wetted Fabric Towel 140 is physically isolated, in a sterile environment in the Inner Sealed Envelope 135, from the heating pouch 130. In the preferred embodiment, the inner sealed envelope 135 is packaged in such a way that it wraps around the heating element pouch 130, thereby capturing more of the thermal energy released by the heating element than would be captured if the inner pouch only contacted one side of the heating element.

In FIG. 2B, this further embodiment provides an option of including at least one, and preferably a plurality of, adhesive bandages 155 within an optional bandage kit 160, for covering surgically-created skin wounds, following cleaning and drying the patient's skin in the area of the surgical field. In the preferred form, the plurality of Adhesive Bandages 155 are each individually wrapped in a paper envelope, in the same way that conventional Band-Aids® are wrapped. For convenience in handling, the Adhesive Bandages 155 may be prepackaged in a suitably sized plastic storage bag. As is typical in bandage 155 embodiments, an absorbent pad is centrally positioned on an Adhesive Bandage 155 and leaving a peripheral area of pressure sensitive adhesive open so that, during use, the pad is secured to the skin of the patient on all sides by the pressure sensitive adhesive surrounding the pad. After the patient's skin is dried with Dry Towel 145, if provided in the kit 100, adhesive bandages 155 may be applied over closed surgical wounds.

Figure 3A:
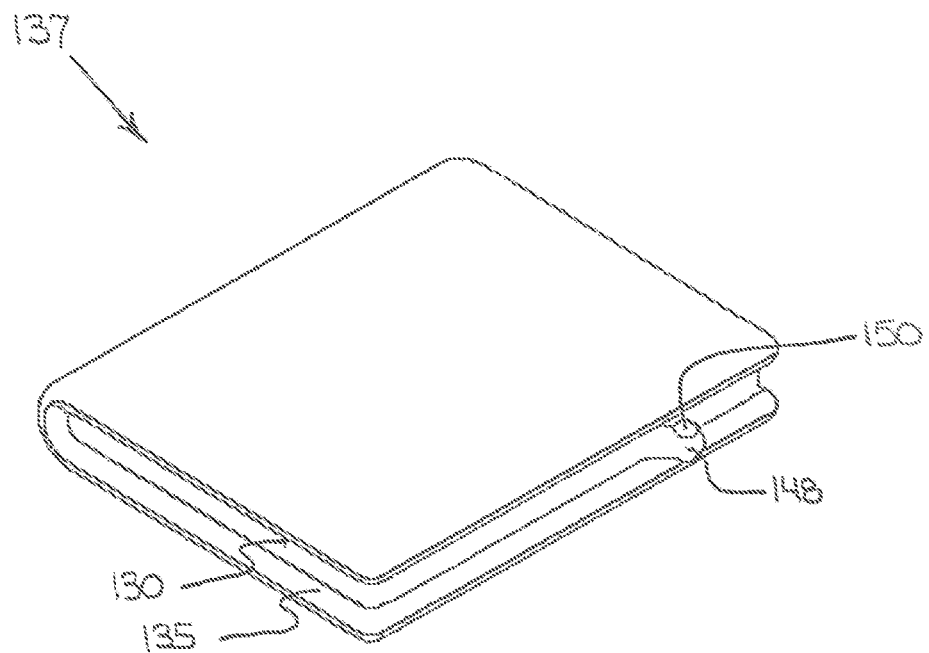
FIG. 3A illustrates a Top Perspective View of the contained Wet Towel Kit.

With respect to FIG. 3A, a Perspective View of the Wetted Fabric Towel Kit 137 is shown. The heating element pouch 130 is shown sandwiched between two folded layers of the Wet Towel kit 137. Once an extended actuating button 150 on tab 148 is pressed to place a metal disc (not shown) into contact with the heating solution, in known manner, the transfer of heat from the heating solution pouch 130 to the sealed Wetted Fabric Towel kit 137 takes place. In this embodiment the extended actuating tab 148 is used but any combination including a kinetic energy generating device may be used to start the nucleation process of the heating solution in the heating element pouch 130.

Figure 3B:
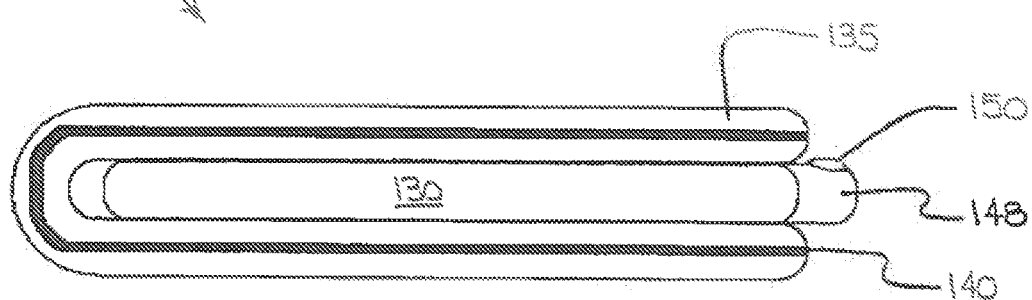
FIG. 3B illustrates a Side Isometric View of the contained Wet Towel Kit.

With respect to FIG. 3B a Side Isometric View of the contained Wet Towel Kit 137 is shown. The elements of the Wet Towel Kit 137, i.e., Wet Towel Inner sealed envelope 135, Wetted Fabric Towel 140 therein, and the heating pouch 130 including Extended Actuating Tab 148, and Extended Actuating button 150, are all shown.

Figure 4A:
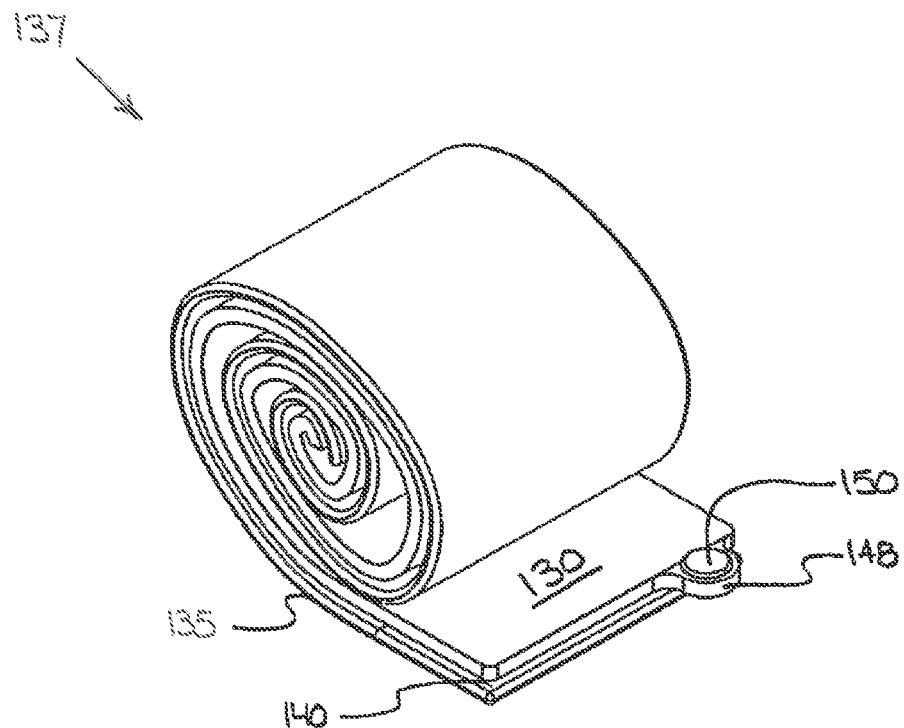
FIG. 4A Illustrates a Top Perspective View of an Alternative Embodiment of the contained Wet Towel Kit, and FIG. 4B Illustrates a side Isometric View of the contained Wet Towel Kit.

With respect to FIG. 4A, a Top Perspective View of a further alternative embodiment of a rolled Wet Towel Kit 137 is shown with the extended actuating tab 148 and extended actuating button 150 of the heating pouch 130 being visible. In this embodiment the Rolled Wet Towel Kit 137, can be held in this circular configuration by various methods including but not limited use of straps, tapes or use of a mechanical holding device. This type of orientation is efficient at transferring heat energy from heating pouch 130 to the Wet Towel 140 within inner envelope 135. Alternative combinations and orientations of the extended actuating tab 148 and the extended actuating button 150 may also be used. In other embodiments, where there is a different type of exothermic chemical reaction, or in embodiments where the heating element is electrically powered, there may be no actuation tab or button used.

Figure 4B:
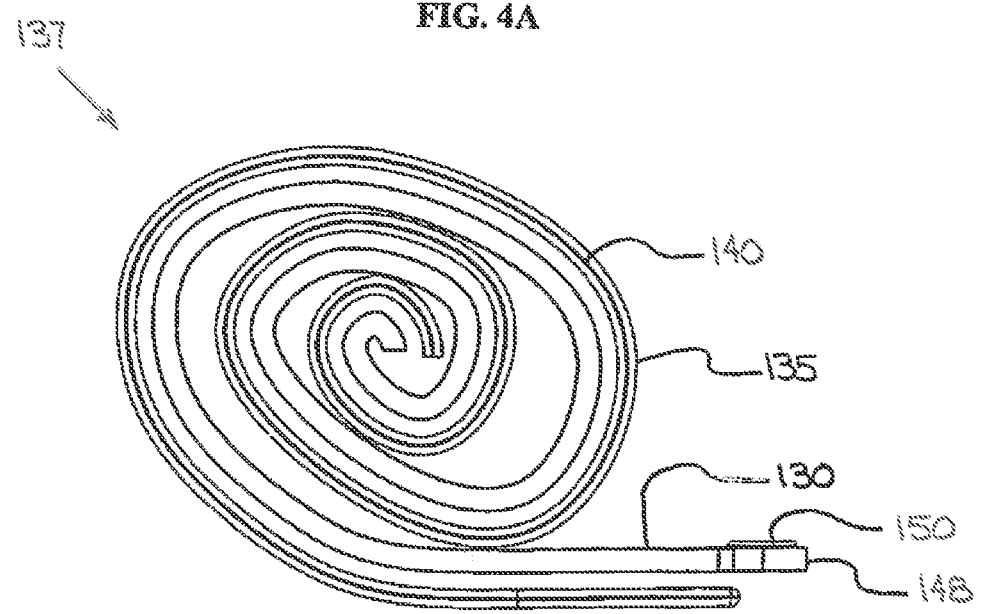

With respect to FIG. 4B an Isometric side view is shown of the rolled Wet Towel Kit 137. The rolling together of the Wet Towel Kit 137 and the heating pouch 130 can take the form of a tight fit or lose fit depending on the desired temperature range. Sterility of the elements is always maintained because the Wet & Dry Kit 100, is not opened until inside a sterile environment, such as an operating room.

The above embodiment may be used as part of a system to provide an effective means of cleaning a patient thru the orderly use of its components. More than one Wet Towel or Dry Towel may be included in the kit. For example, there could be a kit with 2 dry towels and a single wetted towel.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cleaning kit for cleaning a patient's skin in an area requiring removal of contaminants therefrom comprising at least:
    one wetted towel kit comprising a sealed inner envelope containing a wetted fabric towel and a heating pack adapted to heat the wetted fabric towel;
    the heating pack comprising a heating solution and an actuator configured to be activated to cause the heating solution to react exothermically and generate heat;
    the actuator comprising a metal element that is brought into contact with the heating solution when the actuator is activated;
    one dry fabric towel; and
    an outer envelope containing both the at least one sealed inner envelope and the at least one dry fabric towel.

2. The cleaning kit of claim 1 wherein the wetted fabric towel and dry fabric towel are made of a lintless material.

3. The cleaning kit of claim 1 wherein the wetted towel kit contains a solution of saline.

4. The cleaning kit of claim 1 wherein the wetted towel kit contains water.

5. The cleaning kit of claim 1 wherein the wetted towel kit contains a solution containing soap.

6. The cleaning kit of claim 1 wherein the wetted towel kit contains an antibacterial solution.

7. The cleaning kit of claim 1 wherein the wetted fabric towel is folded around the heating pack while leaving the actuator exposed.

8. The cleaning kit of claim 1 wherein the wetted fabric towel is rolled together with the heating pack while still leaving the actuator exposed.

9. The cleaning kit of claim 1 wherein the actuator is an actuating tab.

10. The cleaning kit of claim 1 wherein the actuator is an actuating button.

11. A cleaning kit for cleaning a patient's skin in a surgical field area requiring removal of contaminants therefrom comprising at least:
    one wetted towel kit comprising a sealed inner envelope containing a wetted fabric towel and a heating pouch adapted to heat the wetted fabric towel;
    the heating pouch containing a heating solution and having an actuator configured to be activated to cause the heating solution to react exothermically and generate heat;
    the actuator comprising a metal element that is brought into contact with the heating solution when the actuator is activated;
    one dry fabric towel for drying the patient's skin wetted by the wetted fabric towel; and
    an outer envelope containing both the at least one sealed inner envelope and the at least one dry fabric towel.

12. The cleaning kit of claim 11 wherein the wetted fabric towel and dry fabric towel are made of a lintless material.

13. The cleaning kit of claim 11 wherein the wetted towel kit contains a solution of saline.

14. The cleaning kit of claim 11 wherein the wetted towel kit contains water.

15. The cleaning kit of claim 11 wherein the wetted towel kit contains a solution containing soap.

16. The cleaning kit of claim 11 wherein the wetted towel kit contains an antibacterial solution.

17. The cleaning kit of claim 11 further including sterile bandages.

18. The cleaning kit of claim 11 wherein the wetted fabric towel is folded around the heating pouch while leaving the actuator exposed.

19. The cleaning kit of claim 11 wherein the wetted fabric towel is rolled together with the heating pouch while still leaving the actuator exposed.

20. The cleaning kit of claim 11 wherein the actuator is an actuating tab.

21. The cleaning kit of claim 11 wherein the actuator is an actuating button.

* * * * *